(12) United States Patent
Morschhäuser et al.

(10) Patent No.: US 7,081,507 B2
(45) Date of Patent: Jul. 25, 2006

(54) CATIONICALLY MODIFIED COMB POLYMERS BASED ON ACRYLOYLDIMETHYL TAURINE ACID

(75) Inventors: Roman Morschhäuser, Mainz (DE); Jan Glauder, Frankfurt (DE); Sonja Klein, Hattersheim (DE); Matthias Löffler, Niedernhausen (DE)

(73) Assignee: Clariant GmbH, Frankfurt (DE)

(*) Notice: Subject to any disclaimer, the term of this patent is extended or adjusted under 35 U.S.C. 154(b) by 0 days.

(21) Appl. No.: 10/433,006

(22) PCT Filed: Nov. 28, 2001

(86) PCT No.: PCT/EP01/13856

§ 371 (c)(1),
(2), (4) Date: Nov. 17, 2003

(87) PCT Pub. No.: WO02/44229

PCT Pub. Date: Jun. 6, 2002

(65) Prior Publication Data

US 2005/0032998 A1    Feb. 10, 2005

(30) Foreign Application Priority Data

Dec. 1, 2000   (DE) ................................ 100 59 830

(51) Int. Cl.
*C08F 12/30*   (2006.01)
(52) U.S. Cl. .................... 526/288; 526/287; 526/292.2; 526/292.6; 526/312; 524/458; 524/461
(58) Field of Classification Search ................ 526/287, 526/288, 292.2, 292.6, 312; 524/458, 461
See application file for complete search history.

(56) References Cited

U.S. PATENT DOCUMENTS

| | | | |
|---|---|---|---|
| 4,138,446 A | 2/1979 | Kawakami et al. ......... 260/875 |
| 4,404,111 A | 9/1983 | Bi et al. ................ 252/8.55 D |
| 4,859,458 A | 8/1989 | Salamone et al. |
| 5,160,730 A | 11/1992 | Dubief et al. ................ 424/59 |
| 5,275,809 A | 1/1994 | Chen et al. |
| 5,276,809 A | 1/1994 | Salamone et al. |
| 5,368,850 A | 11/1994 | Cauwet et al. ............... 424/70 |
| 5,639,841 A * | 6/1997 | Jenkins ...................... 526/333 |
| 5,837,789 A | 11/1998 | Stockhausen et al. |
| 5,879,718 A | 3/1999 | Sebillote-Arnaud ........ 424/705 |
| 5,908,618 A | 6/1999 | Lorant ...................... 424/70.5 |
| 6,001,379 A | 12/1999 | Griat ......................... 424/401 |
| 6,120,780 A | 9/2000 | Dupuis et al. ............. 424/401 |
| 6,123,960 A | 9/2000 | Favre et al. ............... 424/450 |
| 6,180,118 B1 | 1/2001 | Maubru ..................... 424/401 |
| 6,395,853 B1 | 5/2002 | Oswald et al. |
| 6,403,074 B1 * | 6/2002 | Blankenburg et al. ... 424/70.12 |
| 6,468,549 B1 | 10/2002 | Dupuis et al. ............. 424/401 |
| 6,645,476 B1 * | 11/2003 | Morschhauser et al. ... 424/70.1 |
| 6,727,318 B1 * | 4/2004 | Mathauer et al. .......... 524/801 |

FOREIGN PATENT DOCUMENTS

| | | |
|---|---|---|
| CA | 2363079 | 8/2000 |
| EP | 0 356 241 | 2/1990 |
| EP | 0 424 260 | 4/1991 |
| EP | 0 603 019 | 6/1994 |
| EP | 0 642 781 | 3/1995 |
| EP | 0 815 828 | 1/1998 |
| EP | 0 815 844 | 1/1998 |
| EP | 0 815 845 | 1/1998 |
| EP | 0 829 258 | 3/1998 |
| EP | 0 850 642 | 7/1998 |
| EP | 0 919 217 | 6/1999 |
| EP | 1069142 | 1/2001 |

OTHER PUBLICATIONS

English Translationof International Preliminary Examination Report, PCT/EP01/13856, Dated Feb. 26, 2003.

* cited by examiner

*Primary Examiner*—Helen L. Pezzuto
(74) *Attorney, Agent, or Firm*—Richard P. Silverman

(57) ABSTRACT

The invention provides water-soluble or water-swellable copolymers obtained by free-radical copolymerization of
A) acryloyldimethyltaurine and/or acryloyldimethyltaurates,
B) optionally, one or more other olefinically unsaturated, noncationic, optionally crosslinking comonomers containing at least one oxygen, nitrogen, sulfur or phosphorus atom and possessing a molecular weight of less than 500 g/mol,
C) one or more mono- or polyolefinically unsaturated, optionally crosslinking macromonomers each possessing at least one oxygen, nitrogen, sulfur or phosphorus atom and having a number-average molecular weight of greater than or equal to 200 g/mol, and
D) one or more olefinically unsaturated, cationic comonomers containing at least one oxygen, nitrogen, sulfur or phosphorus atom and possessing a molecular weight of less than 500 g/mol, the copolymerization
E) taking place in the presence or absence of at least one polymeric additive having number-average molecular weights of from 200 g/mol to $10^9$ g/mol.

The water-soluble or water-swellable copolymers of the present invention are useful in formulating cosmetics.

17 Claims, No Drawings

CATIONICALLY MODIFIED COMB POLYMERS BASED ON ACRYLOYLDIMETHYL TAURINE ACID

The present invention relates to cationically modified comb polymers based on acryloyldimethyltaurine and/or acryloyldimethyltaurates.

Consumer desires and cosmetic product rheology are closely interlinked. For example, the appearance of a cream or lotion is influenced by the viscosity. The sensorial properties, such as consistency or spreadability, determine the individual profile of a cosmetic product. The effectiveness of active substances (e.g., sun protection filters) and also the storage stability of the formulation are closely dependent on the rheological properties of the product.

In cosmetics, polyelectrolytes play a key part as thickeners and gel formers. State of the art are in particular the polyacrylic acids, prepared on the basis of poly(meth)acrylic acid, and the water-soluble copolymers thereof. The diversity of possible structures and the associated diverse possibilities for use are reflected in a host of patent applications.

A substantial disadvantage of thickeners based on poly(meth)acrylic acid is the heavy pH dependence of the thickening effect. Thus, generally speaking, adequate viscosity is only achieved when the pH of the formulation is above 6, i.e., the poly(meth)acrylic acid is in neutralized form. Further, the corresponding gels/formulation are sensitive to UV radiation and shearing and additionally impart a sticky sensation on the skin. Since the thickeners are generally in acidic form, moreover, an additional neutralization step is needed in the course of formulation.

In the 1990s, innovative thickeners based on acryloyldimethyltaurine and/or its salts were introduced into the market (EP-B-0 815 828, EP-B-0 815 844, EP-B-0 815 845, EP-B-0 829 258, EP-A-0 850 642 and EP-A-0 919 217). Both in the form of the preneutralized homopolymer and also as corresponding copolymers (®ARISTOFLEX AVC CLARIANT GmbH) such thickeners are in many respects superior to the poly(meth)acrylate thickeners. For instance, they exhibit an outstanding profile of properties even in pH ranges below pH 6, i.e., a range within which it is no longer possible to operate with conventional poly(meth)acrylate thickeners. High UV stability and shearing stability, outstanding viscoelastic properties, great ease of processing, and a favorable toxicological profile of the principal monomer imbue these thickeners with a high application potential.

The applicant has surprisingly succeeded in obtaining novel cationically modified comb polymers based on acryloyldimethyltaurine (AMPS) which exhibit very good thickening and emulsifying/dispersing properties in combination with high pH stability. In both crosslinked and non-crosslinked form the comb polymers of the invention open up a broad application spectrum. The polymers of the invention put the user for the first time in a position to combine the synergistic properties of hydrophobically modified anionic polymers with the advantages (as is known) of cationic charges.

The invention provides water-soluble or water-swellable copolymers obtainable by free-radical copolymerization of A) acryloyldimethyltaurine and/or acryloyldimethyltaurates, B) if desired, one or more other olefinically unsaturated, noncationic, optionally crosslinking comonomers containing at least one oxygen, nitrogen, sulfur or phosphorus atom and possessing a molecular weight of less than 500 g/mol, C) one or more mono- or polyolefinically unsaturated, optionally crosslinking macromonomers each possessing at least one oxygen, nitrogen, sulfur or phosphorus atom and having a number-average molecular weight of greater than or equal to 200 g/mol, and D) one or more olefinically unsaturated, cationic comonomers containing at least one oxygen, nitrogen, sulfur or phosphorus atom and possessing a molecular weight of less than 500 g/mol, the copolymerization E) taking place in the presence or absence of at least one polymeric additive having number-average molecular weights of from 200 g/mol to $10^9$ g/mol.

The copolymers of the invention preferably possess a molecular weight of from $10^3$ g/mol to $10^9$ g/mol, more preferably from $10^4$ to $10^7$ g/mol, very preferably from $5*10^4$ to $5*10^6$ g/mol.

The acryloyldimethyltaurates can be the organic or inorganic salts of acryloyldimethyltaurine. Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be $(C_1-C_{22})$-alkyl radicals or $(C_2-C_{10})$-hydroxyalkyl radicals. Preference is also given to mono- to triethoxylated ammonium compounds with a different degree of ethoxylation. It should be noted that the invention also embraces mixtures of two or more of the abovementioned representatives.

The degree of neutralization of the acryloyldimethyltaurine can be between 0 and 100%, particular preference being given to a degree of neutralization of more than 80%.

Based on the total mass of the copolymers, the amount of acryloyldimethyltaurine and/or acryloyldimethyltaurates is at least 0.1% by weight, preferably from 20 to 99.5% by weight, more preferably from 50 to 98% by weight.

As comonomers B) it is possible to use all olefinically unsaturated noncationic monomers whose reaction parameters allow copolymerization with acryloyldimethyltaurine and/or acryloyldimethyltaurates in the respective reaction media.

Preferred comonomers B) are unsaturated carboxylic acids and their anhydrides and salts, and also their esters with aliphatic, olefinic, cycloaliphatic, arylaliphatic or aromatic alcohols having a carbon number of from 1 to 22.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions are $Li^+$, $Na^+$, $K^+$, $Mg^{++}$, $Ca^{++}$, $Al^{+++}$, $NH_4^+$, monoalkylammonium, dialkylammonium, trialkylammonium and/or tetraalkylammonium radicals, in which the alkyl substituents of the amines independently of one another can be $(C_1-C_{22})$-alkyl radicals or $(C_2-C_{10})$-hydroxyalkyl radicals. It is additionally possible to employ mono- to triethoxylated ammonium compounds with a different degree of ethoxylation. The degree of neutralization of the carboxylic acids can be between 0 and 100%.

Further preferred comonomers are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide, hydroxyethylmethacrylamide, hydroxypropylmethacrylamide, and mono [2-(methacryloyloxy)ethyl]succinate; N,N-dimethylamino methacrylate; diethylaminomethyl methacrylate; acrylamido- and methacrylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.7% by weight and is preferably from 0.5 to 80% by weight, more preferably from 2 to 50% by weight.

In accordance with the invention at least one so-called macromonomer C) is employed in the copolymerization. The macromonomers are at least singly olefinically functionalized polymers having one or more discrete repeating units and a number-average molecular weight of greater than or equal to 200 g/mol. In the copolymerization it is also possible to use mixtures of chemically different macromonomers C). The macromonomers are polymeric structures composed of one or more repeating units and have a molecular weight distribution characteristic of polymers.

Preferred macromonomers C) are compounds of formula (I).

$R^1$ represents a polymerizable function from the group of the vinylically unsaturated compounds which are suitable for constructing polymeric structures by a free-radical route. Preferably $R^1$ is a vinyl, allyl, methallyl, methylvinyl, acryloyl (CH$_2$=CH—CO—), methacryloyl (CH$_2$=C[CH$_3$]—CO—), crotonyl, senecionyl, itaconyl, maleyl, fumaryl or styryl radical. Attachment of the polymer chain to the reactive end group requires a suitable bridging group Y. Preferred bridges Y are —O—, —C(O)—, —C(O)—O—, —S—, —O—CH$_2$—CH(O—)—CH$_2$OH, —O—CH$_2$—CH(OH)—CH$_2$O—, —O—SO$_2$—O—, —O—SO$_2$—O—, —O—SO—O—, —PH—, —P(CH$_3$)—, —PO$_3$—, —NH—, and —N(CH$_3$)—, more preferably —O—.

The polymeric central moiety of the macromonomer is represented by the discrete repeating units A, B, C, and D. Preferred repeating units A, B, C, and D are derived from acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

The indices v, w, x, and z in formula (I) represent the stoichiometric coefficients relating to the repeating units A, B, C, and D. v, w, x, and z amount independently of one another to from 0 to 500, preferably 1 to 30, it being necessary for the sum of the four coefficients on average to be $\geq 1$.

The distribution of the repeating units over the macromonomer chain can be random, blocklike, alternating or gradientlike.

$R^2$ denotes a linear or branched aliphatic, olefinic, cycloaliphatic, arylaliphatic or aromatic (C$_1$–C$_{50}$) hydrocarbon radical, OH, —NH$_2$, —N(CH$_3$)$_2$ or is the structural unit [—Y—R$^1$].

In the case of $R^2$ being [—Y—R$^1$] the macromonomers in question are difunctional and suitable for crosslinking the copolymers.

Particularly preferred macromonomers C) are acrylically or methacrylically monofunctionalized alkyl ethoxylates of formula (II).

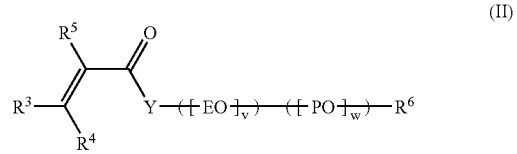

$R^3$, $R^4$, $R^5$, and $R^6$ are independently of one another hydrogen or n-aliphatic, isoaliphatic, olefinic, cycloaliphatic, arylaliphatic or aromatic (C$_1$–C$_{30}$) hydrocarbon radicals.

Preferably $R^3$ and $R^4$ are H or —CH$_3$, more preferably H; $R^5$ is H or —CH$_3$; and $R^6$ is an n-aliphatic, iso-aliphatic, olefinic, cycloaliphatic, arylaliphatic or aromatic (C$_1$–C$_{30}$) hydrocarbon radical.

v and w are in turn the stoichiometric coefficients relating to the ethylene oxide units (EO) and propylene oxide units (PO). v and w amount independently of one another to from 0 to 500, preferably 1 to 30, it being necessary for the sum of v and w to be on average $\geq 1$. The distribution of the EO and PO units over the macromonomer chain can be random, blocklike, alternating or gradientlike. Y stands for the above-mentioned bridges.

Particularly preferred macromonomers C) have the following structure in accordance with formula (II):

| Name | $R^3$ | $R^4$ | $R^5$ | $R^6$ | V | W |
|---|---|---|---|---|---|---|
| ® LA-030 methacrylate | H | H | —CH$_3$ | -lauryl | 3 | 0 |
| ® LA-070 methacrylate | H | H | —CH$_3$ | -lauryl | 7 | 0 |
| ® LA-200 methacrylate | H | H | —CH$_3$ | -lauryl | 20 | 0 |
| ® LA-250 methacrylate | H | H | —CH$_3$ | -lauryl | 25 | 0 |
| ® T-080 methacrylate | H | H | —CH$_3$ | -talc | 8 | 0 |
| ® T-080 acrylate | H | H | H | -talc | 8 | 0 |
| ® T-250 methacrylate | H | H | —CH$_3$ | -talc | 25 | 0 |
| ® T-250 crotonate | —CH$_3$ | H | —CH$_3$ | -talc | 25 | 0 |
| ® OC-030 methacrylate | H | H | —CH$_3$ | -octyl | 3 | 0 |
| ® OC-105 methacrylate | H | H | —CH$_3$ | -octyl | 10 | 5 |
| ® Behenyl-010-methylaryl | H | H | H | -behenyl | 10 | 0 |
| ® Behenyl-020-methylaryl | H | H | H | -behenyl | 20 | 0 |
| ® Behenyl-010-senecionyl | —CH$_3$ | —CH$_3$ | H | -behenyl | 10 | 0 |
| ® PEG-440 diacrylate | H | H | H | -acryloyl | 10 | 0 |
| ® B-11-50 methacrylate | H | H | —CH$_3$ | -butyl | 17 | 13 |
| ® MPEG-750 methacrylate | H | H | —CH$_3$ | -methyl | 18 | 0 |
| ® P-010 acrylate | H | H | H | -phenyl | 10 | 0 |
| ® O-050 acrylate | H | H | H | -oleyl | 5 | 0 |

The molecular weight of the macromonomers C) is preferably from 200 g/mol to 10$^6$ g/mol, more preferably from 150 to 10$^4$ g/mol, and very preferably from 200 to 5 000 g/mol.

The weight fraction of the macromonomer F), based on the total mass of the copolymers, is from 0.1 to 99.8% by weight, more preferably from 2 to 90% by weight, and very preferably from 5 to 80% by weight.

Essential to the invention is that the copolymers include in their structure at least one cationic comonomer D). Suitable comonomers D) include all olefinically unsaturated monomers with cationic charge which are capable of forming copolymers with acryloyldimethyltaurine or its salts in the chosen reaction media. The resulting distribution of the cationic charges across the chains can be random, alternating, blocklike or gradientlike. It may be noted that the cationic comonomers D) also comprehend those which bear the cationic charge in the form of a betaine structure. Comonomers D) for the purposes of the invention are also amino-functionalized precursors which can be converted into their corresponding quaternary derivatives by polymer-analogous reactions (e.g., reaction with DMS).

Particularly preferred comonomers D) are diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride and/or
N-methyl4-vinylpyridinium chloride.

The weight fraction of the comonomers D), based on the total mass of the copolymers, is preferably from 0.1 to 99.8% by weight, more preferably from 0.5 to 30% by weight, and very preferably from 1 to 20% by weight.

In one other preferred embodiment the copolymerization is conducted in the presence of at least one polymeric additive E), the additive E) being added wholly or partly in solution to the polymerization medium before the actual copolymerization. The use of two or more additives E) is likewise in accordance with the invention. Crosslinked additives E) may likewise be used.

The additives E) or mixtures thereof must only be wholly or partly soluble in the chosen polymerization medium.

During the actual polymerization step the additive E) has a number of functions. On the one hand it prevents the formation of overcrosslinked polymer fractions in the copolymer which forms in the actual polymerization step, and on the other hand the additive E) is statistically attacked by active free radicals in accordance with the very well-known mechanism of graft copolymerization. Depending on the particular additive E), this results in greater or lesser fractions of the additive being incorporated into the copolymers. Moreover, suitable additives E) possess the property of altering the solution parameters of the copolymers which form during the free-radical polymerization reaction in such a way that the average molecular weights are shifted to higher values. As compared with analogous copolymers prepared without the addition of the additives E), those prepared with the addition of additives E) advantageously exhibit a significantly higher viscosity in aqueous solution.

Preferred additives E) are homopolymers and copolymers which are soluble in water and/or alcohols. The term "copolymers" also comprehends those having more than two different monomer types.

Particularly preferred additives E) are homopolymers and copolymers of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy)ethyl]trimethylammonium chloride (MAPTAC); polyalkylene glycols and/or alkylpolyglycols.

Particularly preferred additives E) are polyvinylpyrrolidones (e.g., K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives E) is preferably from $10^2$ to $10^7$ g/mol, more preferably from $0.5*10^4$ to $10^6$ g/mol.

The amount in which the polymeric additive E) is used, based on the total mass of the monomers to be polymerized during the copolymerization, is preferably from 0.1 to 90% by weight, more preferably from 1 to 20% by weight, and with particular preference from 1.5 to 10% by weight.

In one further preferred embodiment the copolymers of the invention are crosslinked, i.e., they contain comonomers containing at least two polymerizable vinyl groups.

Preferred crosslinkers are methylenebisacrylamide; methylenebismethacrylamide; esters of unsaturated monocarboxylic and polycarboxylic acids with polyols, preferably di-acrylates and triacrylates and -methacrylates, more preferably butanediol and ethylene glycol diacrylate and -methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives.

A particularly preferred crosslinker is trimethylolpropane triacrylate (TMPTA).

The weight fraction of crosslinking comonomers, based on the total mass of the copolymers, is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electro-magnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide or azo initiators, such as azodiisobutyronitrile (AIBN), for example. Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

The polymerization reaction can be conducted, for example, as a precipitation polymerization, emulsion polymerization, bulk polymerization, solution polymerization or gel polymerization. Particularly advantageous for the profile of properties of the copolymers of the invention is precipitation polymerization, preferably in tert-butanol.

The polyfunctional polymers of the invention possess a great structural diversity and, consequently, broad potential possibilities for use, which can be tailored to virtually any task where interface effects and/or surface effects play a part. The term "custom-tailored polymers" gives a vivid description of the possibilities which this new class of polymer affords the user.

The presence of cationic charges in the polymer framework makes it possible to make purposive exploitation of adhesion effects in relation to anionic surfaces. The combination of basic properties which are in some cases completely contradictory, such as, for example, water solubility and oil solubility or anionic and cationic charges in one single molecule, opens up the path to water-soluble association polymers having completely new kinds of profiles of properties. An example that will be given at this point is the strikingly high electrolyte stability of thickener systems based on the copolymers of the invention, allowing them to be used as "superabsorbents" for electrolyte-containing solutions. This is in contrast to the low salt stability of many water-absorbing hygiene articles based on crosslinked, fully or partly neutralized polyacrylic acids.

The following examples are intended to illustrate the invention without, however, restricting it thereto.

EXAMPLE 1

| Reactants | amount (g) |
| --- | --- |
| $NH_3$-neutralized AMPS | 80 |
| ® Genapol-BE-010 methacrylate | 15 |
| DADMAC | 5 |
| t-Butanol | 400 |
| Dilauroyl peroxide (initiator) | 1 |

The polymer was prepared by the precipitation method in tert-butanol. The monomers in t-butanol were introduced as an initial charge, the reaction mixture was rendered inert, and then, after initial heating to 60° C., the reaction was initiated by addition of DLP. The polymer was isolated by removal of the solvent under suction and by subsequent vacuum drying.

The polymer in 1% strength solution in distilled water gave a viscosity of 11 000 mPas.

EXAMPLE 2

| Reactants | amount (g) |
| --- | --- |
| $NH_3$-neutralized AMPS | 70 |
| N-Vinylpyrrolidone | 5 |
| ® Genapol-T-250 methacrylate | 15 |
| [2-(Methacryloyloxy)ethyl]trimethylammonium chloride | 10 |
| Water | 500 |
| $Na_2S_2O_8$ (initiator) | 1 |
| Poly-N-vinylpyrrolidone (® K-15, BASF) | 4 |

The polymer was prepared by the gel polymerization method in water. The monomers were dissolved in water, the reaction mixture was rendered inert, and then, after initial heating to 70° C., the reaction was initiated by addition of sodium peroxodisulfate. The polymer gel was subsequently comminuted and the polymer was isolated by vacuum drying.

EXAMPLE 3

| Reactants | amount (g) |
| --- | --- |
| AMPS | 80 |
| ® Genapol-T-250 methacrylate | 20 |
| [2-(Methacrylamido)ethyl]trimethylammonium chloride | 25 |
| Cyclohexane | 200 |
| Water | 300 |
| ® Span 80 | 1 |
| $Na_2S_2O_8$ (initiator) | 1 |

The polymer was prepared by the emulsion method in water. The monomers were emulsified in water/cyclohexane using Span 80®, the reaction mixture was rendered inert using $N_2$, and then, after initial heating to 60° C., the reaction was initiated by addition of sodium peroxodisulfate. The polymer emulsion was subsequently evaporated down (cyclohexane acting as azeotrope former for water) and the polymer was isolated.

EXAMPLE 4

| Reactants | amount (g) |
| --- | --- |
| $NH_3$-neutralized AMPS | 80 |
| MPEG-750 methacrylate | 15 |
| N-Methyl-4-vinylpyridinium chloride | 5 |
| t-Butanol | 300 |
| TMPTA | 1.8 |
| AIBN (initiator) | 1 |

The polymer was prepared by the precipitation method in tert-butanol. The monomers in t-butanol were introduced as an initial charge, the reaction mixture was rendered inert, and then, after initial heating to 68° C., the reaction was initiated by addition of AIBN. The polymer was isolated by removal of the solvent under suction and by subsequent vacuum drying.

EXAMPLE 5

| Reactants | amount (g) |
| --- | --- |
| Na-neutralized AMPS | 80 |
| MPEG-750 methacrylate | 15 |
| ® Genapol-O-150 methacrylate | 15 |
| [2-(Methacryloyloxy)ethyl]trimethylammonium chloride | 5 |
| DADMAC | 5 |
| Water | 300 |
| $H_2O_2$/iron (initiator) | 1 |
| Poly[N-vinylcaprolactam] | 5 |

The polymer was prepared by the solution method in water. The monomers were dissolved in water, the reaction mixture was rendered inert, and then, after initial heating to 55° C., the reaction was initiated by means of an iron(II) sulfate/$H_2O_2$ redox couple. The polymer solution was subsequently evaporated down and the polymer was then isolated by vacuum drying.

EXAMPLE 6

| Reactants | amount (g) |
|---|---|
| NH$_3$-neutralized AMPS | 80 |
| ® Genapol-LA-040 methacrylate | 20 |
| [2-(Acrylamido)ethyl]trimethylammonium chloride | 25 |
| t-Butanol | 500 |
| TMPTA | 1.8 |
| Dilauroyl peroxide | 2 |
| Poly[N-vinylformamide] | 1 |

The polymer was prepared by the precipitation method in tert-butanol. The monomers in t-butanol were introduced as an initial charge, the reaction mixture was rendered inert, and then, after initial heating, the reaction was initiated by addition of DLP. The polymer was isolated by removal of the solvent under suction and by subsequent vacuum drying.

Chemical Designation of the Products Employed

| | |
|---|---|
| TMPTA | Trimethylolpropane triacrylate |
| AIBN | Azoisobutyronitrile |
| DLP | Dilauroyl peroxide |
| ® Genapol-T-250 methacrylate | Methacrylic acid C$_{16}$/C$_{18}$ alcohol ethoxylate ester |
| ® Genapol-LA-070 methacrylate | Methacrylic acid C$_{12}$/C$_{14}$ alcohol ethoxylate ester (7EO) |
| NH$_3$-neutralized AMPS | 2-Acrylamido-2-methyl-1-amidopropanesulfonic acid (ammonium salt) |
| ® Span 80 | Sorbitan ester |
| MPEG-750 methacrylate | Methacrylic acid methyl ethoxylate ester (750 g/mol) |
| ® Genapol-O-150 methacrylate | Methacrylic acid oleyl ethoxylate ester |
| ® Genapol-LA-250 methacrylate | Methacrylic acid C$_{12}$/C$_{14}$ alcohol ethoxylate ester (25EO) |
| ® Genapol-LA-030 methacrylate | Methacrylic acid C$_{12}$/C$_{14}$ alcohol ethoxylate ester (3EO) |
| ® Genapol-LA-040 methacrylate | Methacrylic acid C$_{12}$/C$_{14}$ alcohol ethoxylate ester (4EO) |

What is claimed is:

1. A water-soluble or water-swellable copolymer obtained by free-radical copolymerization of
   A) 50 to 99.5% by weight of acryloyldimethyltaurine and/or acryloyldimethyltaurate based on a total weight of said copolymer, said acryloyldimethyltaurine and/or acryloyldimethyltaurate having a degree of neutralization of more than 80%,
   B) optionally, one or more other olefinically unsaturated, noncationic, comonomer containing at least one oxygen, nitrogen, sulfur or phosphorus atom and having a molecular weight of less than 500 g/mol,
   C) one or more mono- or polyolefinically unsaturated, macromonomer each having at least one oxygen, nitrogen, sulfur or phosphorus atom and having a number-average molecular weight of greater than or equal to 200 g/mol, and
   D) one or more olefinically unsaturated, cationic comonomer containing at least one oxygen, nitrogen, sulfur or phosphorus atom and having a molecular weight of less than 500 g/mol, the copolymerization
   E) taking place in the absence of at least one polymeric additive having number-average molecular weights of from 200 g/mol to 10$^9$ g/mol.

2. The water-soluble or water-swellable copolymer as claimed in claim 1, wherein the macromonomer C) is of the formula (I)

$$R^1-Y-[(A)_v-(B)_w-(C)_x-(D)_z]-R^2 \qquad (I)$$

where R$^1$ a polymerizable function from a vinylically unsaturated compound;

Y is a bridging group;

A, B, C, and D independently of one another are discrete chemical repeating units;

v, w, x, and z independently of one another amount to from 0 to 500, the sum of v, w, x, and z being on average $\geq 1$; and R$^2$ is a linear or branched aliphatic, olefinic, cycloaliphatic, arylaliphatic or aromatic (C$_1$-C$_{50}$) hydrocarbon radical, OH, —NH$_2$ or —N(CH$_3$)$_2$ or is [—Y—R$^1$].

3. The water-soluble or water-swellable copolymer as claimed in claim 2, wherein the macromonomer C) a compound of formula (II)

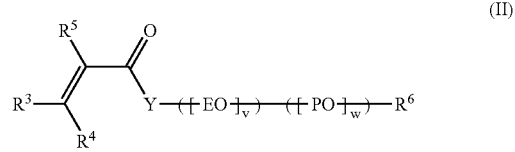

in which R$^3$, R$^4$, R$^5$, and R$^6$ are independently of one another hydrogen, n-aliphatic, iso-aliphatic, cycloaliphatic, olefinic, arylaliphatic and/or aromatic radicals having a carbon number of from 1 to 30, EO is an ethylene oxide unit, and PO is a propylene oxide unit, and v and w independently of one another are from 0 to 500, the sum of v and w being on average $\geq 1$.

4. The water-soluble or water-swellable copolymer of claim 1, wherein the comonomer D) is selected from the group consisting of diallyldimethylammonium chloride,

[2-(methacryloyloxy)ethyl]trimethylammonium chloride,

[2-(acryloyloxy)ethyl]trimethylammonium chloride,

[2-methacrylamidoethyl]trimethylammonium chloride,

[2-(acrylamido)ethyl]trimethylammonium chloride,

N-methyl-2-vinylpyridinium chloride,

N-methyl-1-vinylpyridinium chloride, and mixtures thereof.

5. The water-soluble or water-swellable copolymer of claim 1, further comprising one or more comonomer B).

6. The water-soluble or water-swellable copolymer as claimed in claim 5, wherein the comonomer B) is selected from the group consisting of unsaturated carboxylic acids, salts of unsaturated carboxylic acids, anhydrides of unsaturated carboxylic acids, esters of unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate; styrene, acrylonitrile, vinyl chloride, vinylidene chloride, tetrafluoroethylene, vinylphosphonic acid or the esters or salts thereof, vinylsulfonic acid or the esters or salts thereof, allylphosphonic acid or the esters or salts thereof, methallylsulfonic acid or the esters or salts thereof, and mixtures thereof.

7. The water-soluble or water-swellable copolymer as claimed in claim 1, wherein the polymeric additive E) is selected from the group consisting of polyalkylene glycol, alkylpolyglycol, and mixtures thereof or a homopolymer or copolymer of a compound selected from the group consisting of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxymethyl methacrylate, diallyldimethylammonium chloride (DADMAC), [2-(methacryloyloxy)ethyl] trimethylammonium chloride (MAPTAC), and mixtures thereof.

8. The water-soluble or water-swellable copolymer of claim 1, which is crosslinked.

9. The water-soluble or water-swellable copolymer of claim 1, wherein the copolymer is copolymerized by precipitation polymerization in tert-butanol.

10. The water-soluble or water-swellable copolymer of claim 2, wherein $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

11. The water-soluble or water-swellable copolymer of claim 2, wherein the chemical bridge Y is selected from the group consisting of O—, —S—, —C(O)—, —C(O)—O—, —O—CH$_2$—CH(O—)—CH$_2$OH, —O—CH$_2$—CH(OH)—CH$_2$O—, —O—SO$_2$—O—, —O—SO$_2$—O—, —O—SO—O—, —PH—, —P(CH$_3$)—, —PO$_3$—, —NH—, —N(CH$_3$), and mixtures therefore.

12. The water-soluble or water-swellable copolymer of claim 2, wherein the repeating units A, B, C, and D originate from the group consisting of acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, diisopropylacrylamide, and mixtures thereof.

13. The water-soluble or water-swellable copolymer of claim 2, wherein the repeating units A, B, C, and D originate from ethylene oxide and/or propylene oxide.

14. The water-soluble or water-swellable copolymer of claim 2, wherein v, w, x, and z independently of one another amount to from 1 to 30.

15. The water-soluble or water-swellable copolymer of claim 3, wherein v and w independently of one another amount to from 1 to 30.

16. A water-soluble or water-swellable copolymer obtained by free-radical copolymerization of 50 to 99.5% by weight of acryloyldimethyltaurine and/or acryloyldimethyltaurate based on a total weight of said copolymer, said acryloyldimethyltaurine and/or acryloyldimethyltaurate having a degree of neutralization of more than 80%, with or in the presence of at least one component selected from the group consisting of:
   a) one or more polyolefinically unsaturated, macromonomer each having at least one oxygen, nitrogen, sulfur or phosphorus atom and having a number-average molecular weight of greater than or equal to 200 g/mol, and
   b) one or more olefinically unsaturated, cationic comonomer containing at least one oxygen, nitrogen, sulfur or phosphorus atom and having a molecular weight of less than 500 g/mol,
   c) said copolymerization taking place in the absence of at least one polymeric additive having number-average molecular weights of from 200 g/mol to $10^9$ g/mol.

17. The water-soluble or water-swellable copolymer of claim 16, further comprising one or more olefinically unsaturated, noncationic comonomer containing at least one oxygen, nitrogen, sulfur or phosphorus atom and having a molecular weight of less than 500 g/mol.

\* \* \* \* \*